United States Patent [19]

Ueno

[11] Patent Number: 6,156,910
[45] Date of Patent: Dec. 5, 2000

[54] ε-CAPROLACTONE, PROCESS FOR PRODUCING THE SAME, POLYCAPROLACTONE OBTAINED THEREFROM, AND PROCESS FOR PRODUCING THE POLYCAPROLACTONE

[75] Inventor: Takashi Ueno, Ohtake, Japan

[73] Assignee: Daicel Chemical Industries, Ltd., Osaka, Japan

[21] Appl. No.: 09/380,150

[22] PCT Filed: Dec. 25, 1998

[86] PCT No.: PCT/JP98/05957

§ 371 Date: Nov. 29, 1999

§ 102(e) Date: Nov. 29, 1999

[87] PCT Pub. No.: WO99/33819

PCT Pub. Date: Jul. 8, 1999

[30] Foreign Application Priority Data

Dec. 26, 1997 [JP] Japan ..................................... 9-366978

[51] Int. Cl.[7] .................................................. C07D 313/00
[52] U.S. Cl. .............................................................. 549/266
[58] Field of Search ................................................ 549/266

[56] References Cited

U.S. PATENT DOCUMENTS 4,313,879  2/1982  Klenk et al. ............................ 549/266

*Primary Examiner*—Amelia Owens
*Attorney, Agent, or Firm*—Morgan & Finnegan, L.L.P.

[57] ABSTRACT

The present invention provides ε-caprolactone having a purity of at least 99.8% by weight and a total concentration of not more than 200 ppm based on area ratio of components having a relative retention time of not more than 0.6 (low-boiling fraction), the relative retention time of ε-caprolactone being set to 1.00 in gas-chromatographic analysis under determined conditions. The present invention also provides a method of producing ε-caprolactone consisting of co-oxidizing cyclohexanone and aldehyde(s) or oxidizing cyclohexanone using a peracid to obtain ε-caprolactone and carboxylic acid(s) and recovering the ε-caprolactone via distillation after addition of an element selected from 4A, 5A, 6A, 7A, 8, 1B and 2B groups and/or a compound containing such an element.

9 Claims, 2 Drawing Sheets

| PKNO | TIME | AREA | MK | IDNO | CONC | NAME |
|---|---|---|---|---|---|---|
| 1 | 1.557 | 274 | | | 0.0016 | |
| 2 | 1.618 | 139 | V | | 0.0038 | |
| 3 | 2.098 | 2249 | SV | | 0.0133 | |
| 4 | 2.441 | 211 | T | | 0.0013 | |
| 5 | 2.552 | 559 | V | | 0.0033 | |
| 6 | 3.262 | 200 | | | 0.0012 | |
| 7 | 3.482 | 229 | | | 0.0014 | |
| 8 | 3.63 | 555 | V | | 0.0033 | |
| 9 | 4.15 | 550 | V | | 0.0033 | |
| 10 | 4.588 | 207 | V | | 0.0012 | |
| 11 | 4.7 | 199 | V | | 0.0012 | |
| 12 | 5.285 | 174 | | | 0.001 | |
| 13 | 5.413 | 3490 | V | | 0.0207 | |
| 14 | 5.63 | 4341 | V | | 0.0258 | |
| 15 | 6.27 | 268 | | | 0.0016 | |
| 16 | 8.462 | 16833082 | | | 99.8842 | |
| 17 | 8.94 | 188 | | | 0.0011 | |
| 18 | 9.077 | 609 | V | | 0.0036 | |
| 19 | 9.381 | 423 | | | 0.0025 | |
| 20 | 10.013 | 1258 | | | 0.0075 | |
| 21 | 11.66 | 990 | | | 0.0059 | |
| 22 | 12.078 | 271 | V | | 0.0016 | |
| 23 | 13.629 | 2128 | | | 0.0126 | |
| TOTAL | | 16852586 | | | 100 | |

| PKNO | TIME | AREA | MK | IDNO | CONC | NAME |
|------|------|------|----|------|------|------|
| 1 | 1.57 | 195 | | | 0.0012 | |
| 2 | 2.103 | 1442 | SV | | 0.0089 | |
| 3 | 2.556 | 588 | | | 0.0036 | |
| 4 | 3.518 | 1693 | | | 0.0104 | |
| 5 | 3.609 | 617 | V | | 0.0038 | |
| 6 | 4.587 | 158 | | | 0.001 | |
| 7 | 4.739 | 1034 | V | | 0.0064 | |
| 8 | 5.433 | 210 | | | 0.0013 | |
| 9 | 5.627 | 474 | | | 0.0029 | |
| 10 | 8.448 | 16219568 | | | 99.9378 | |
| 11 | 8.571 | 1263 | V | | 0.0078 | |
| 12 | 9.042 | 1931 | V | | 0.0119 | |
| 13 | 9.602 | 228 | V | | 0.0014 | |
| 14 | 13.605 | 270 | | | 0.0017 | |
| TOTAL | | 16229651 | | | 100 | |

ε-CAPROLACTONE, PROCESS FOR PRODUCING THE SAME, POLYCAPROLACTONE OBTAINED THEREFROM, AND PROCESS FOR PRODUCING THE POLYCAPROLACTONE

TECHNICAL FIELD

The present invention relates to an ε-caprolactone which has excellent thermal-discoloration resistance properties and to a method of producing thereof. The present invention also relates to a polycaprolactone having low discolorability and which is obtained by using the ε-caprolactone, and to a method of producing thereof.

TECHNICAL BACKGROUND

A method consisting of oxidising cyclohexanone is typically known as a method of producing ε-caprolactone.

The method of oxidising the cyclohexanone is a method of cooxidation using aldehyde(s) or a method using organic peroxides as oxidising agent.

Peracetic acid, perpropionic acid, perisobutyric acid or the like are used as the organic peracids.

Acetaldehyde, benzaidehyde, alkyl-substituted benzaldehydes or the like are used as aldehydes for the co-oxidation.

The synthesised carboxylic acids may, for example, in case of aliphatic carboxylic acids be directly used as products for industrial use; in case of aromatic carboxylic acids, they can be transformed through a further oxidation into adipic acids or the like.

ε-caprolactone is polymerised and then used as a moulding material, for polyester polyols, for biodegradable plastics or the like. However, during polymer production, there is an influence on the polymerisation reaction, and there are risks of obtaining discoloured resins. This is due to the great influence of the impurities contained in the ε-caprolactone on the reaction rate and on the colour hue of the polymer. Particularly, the content of the small amount of impurities contained in the ε-caprolactone, the acid value thereof, the water content thereof or the like should be optionally reduced, since they have an influence on the polymerisation reaction-rate, on the value obtained at the thermal discoloration stability test (APHA) of the ε-caprolactone itself and on the colour hue (APHA) of the resins obtained after polymerisation.

Consequently, the purpose of the present invention is to provide an ε-caprolactone which presents few discoloration risks during monomer formation/storage and during polymer formation as well as use thereof and to provide a method of producing such an ε-caprolactone. The purpose of the invention is also to provide polycaprolactone(s) having low discolorability by using the ε-caprolactone and to provide a method of producing these polycaprolactones.

DISCLOSURE OF THE INVENTION

As a result of investigations concerning compounds being factors of the above-mentioned discoloration, the inventor of the present invention has discovered how to obtain ε-caprolactone having improved storage-discoloration resistance and thermal-discoloration resistance via increasing the purity of ε-caprolactone up to 99.8% by weight and reducing the amount of specific impurities until a determined level and via treating the discoloration agents by distillation after addition of a specific element of the 4A group or a compound containing this element. Further, it has been discovered that polycaprolactone(s) having improved color hue can be produced by using the above-mentioned ε-caprolactone.

In other words, the first aspect of the invention provides caprolactone having a purity of at least 99.8% by weight and having a total concentration of not more than 200 ppm based on area ratio of components having a relative retention time of not more than 0.6 (low-boiling components), the relative retention time of ε-caprolactone being set to 1.00 in a gas-chromatographic analysis under determined conditions.

The second aspect of the invention provides ε-caprolactone having a purity of at least 99.8% by weight and having a total concentration of not more than 200 ppm based on area ratio of components having a relative retention time of not more than 0.6 (low-boiling components) and total concentration from 100 to 1,000 ppm based on area ratio of components having a relative retention time of more than 0.6 and less than 1.0 (middle-boiling components), the relative retention time of ε-caprolactone being set to 1.00 in a gas-chromatographic analysis under determined conditions.

The third aspect of the invention provides ε-caprolactone having a purity of at least 99.8% by weight and having a total concentration of not more than 200 ppm based on area ratio of components having a relative retention time of less than 0.6 (low-boiling components), a total concentration of 300 to 1,000 ppm based on area ratio of components having a relative retention time of more than 1.0 and less than 2.0 (high-boiling components), the relative retention time of ε-caprolactone being set to 1.00 in a gas-chromatographic analysis under determined conditions.

The fourth aspect of the invention provides ε-caprolactone according to any one of the first, the second and the third aspect of the invention and having a thermal discoloration of not more than APHA 25, under determined conditions.

The fifth aspect of the invention provides ε-caprolactone described in any one of the above aspects wherein ε-caprolactone is obtained by co-oxidation of cyclohexanone and aromatic aldehyde(s) or by oxidation of cyclohexanone with a peracid.

The sixth aspect of the invention provides a method of producing ε-caprolactone consisting of co-oxidising cyclohexanone and aldehyde(s) to obtain ε-caprolactone and carboxylic acid and then recovering ε-caprolactone via distillation, under controlled degree of reduced pressure and heating in order to obtain ε-caprolactone having a purity of at least 99.8% by weight and having a total concentration of not more than 200 ppm based on area ratio of components having a relative retention time of not more than 0.6 (low-boiling components), the relative retention time of ε-caprolactone being set to 1.00 in a gas-chromatographic analysis under determined conditions.

The seventh aspect of the invention provides a method of producing ε-caprolactone consisting in co-oxidising cyclohexanone and aldehyde(s) or oxidising cyclohexanone using a peracid to obtain ε-caprolactone and carboxylic acid(s) and recovering the ε-caprolactone via distillation after addition of an element selected from 4A, 5A, 6A, 7A, 8, 1B and 2B groups and/or a compound containing such an element.

The eighth aspect of the present invention provides a polycaprolactone having a low discolorability value of not more than APHA 40 and obtained by polymerisation of ε-caprolactone according to any one of the first to the seventh aspects of the invention.

The ninth aspect of the invention provides a method of producing a polycaprolactone having a low discolorability value of not more than APHA 40 by polymerising ε-caprolactone according to any one of the first to the seventh aspects of the invention, in the presence of an initiator and a catalyst.

According to the present invention, it is possible to obtain 6caprolactone having excellent thermal-discoloration resistance. Further, it is possible to synthesise a polycaprolactone having a good color hue from ε-caprolactone obtained according to the present invention.

BEST MODE FOR CARRYING OUT THE INVENTION

Figure 1:
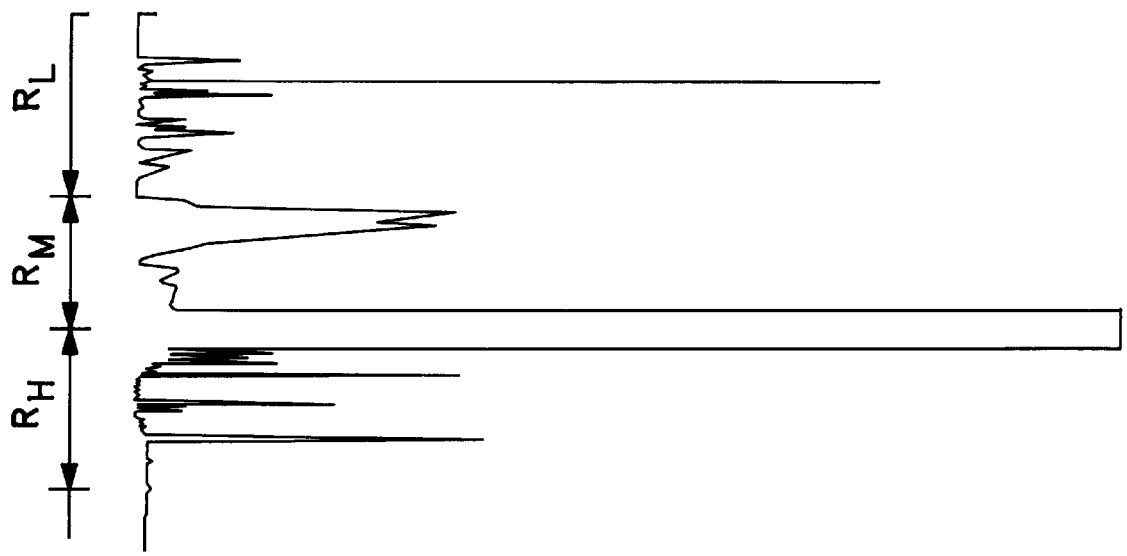
FIG. 1 shows a gas chromatograph chart of the ε-caprolactone product of Example I-1.

The present invention will be explained in more detail hereinafter.

In the present invention, a low-boiling component is a component showing a relative retention time of not more than 0.6 in gas chromatographic analysis under fixed condition whereas the relative retention time of ε-caprolactone, under the same conditions is 1.00. When the relative retention time is more than 0.6 and less than 1.0, the component is said to be a middle-boiling component and when the retention time is more than 1.0 and less than 2.0, the corresponding component is said to be a high-boiling component.

In the present invention, the low-boiling fraction is the fraction having, in distillation, a boiling point lower than the boiling point of ε-caprolactone; the high-boiling fraction is the fraction having a boiling point higher than the boiling point of ε-caprolactone.

The relationship between the low-boiling components in gas chromatography and the low-boiling fraction in distillation is not always evident.

The methods consisting of oxidising cyclohexanone are typically known as a method of producing ε-caprolactone.

As an oxidation of cyclohexanone, there is an oxidising method using organic peracids as oxidising agent and a method of aldehyde(s) co-oxidation using molecular-state oxygen.

Performic acid, peracetic acid, perpropionic acid, perisobutyric acid or other aliphatic percarboxylic acids having 1 to 10 carbons (apart from the carboxylic group, hereinafter the same), aromatic percarboxylic acids having 6 to 10 carbons such as aromatic peracids, methyl substituted aromatic peracids, dimethyl-substituted aromatic peracids may be given as examples of organic peracids. They may also be used as an equilibrium peracid mixture of hydrogen peroxide or other peroxidised compound.

Formaldehyde, acetaldehyde, propionaidehyde or other aliphatic aldehydes having 1 to 10 carbons (apart from the aldehyde group, hereinafter the same), benzaldehyde, methyl-substitued benzaldehyde, dimethyl-substituted benzaldehyde or other aromatic aldehydes having 6 to 10 carbons may be used as aldehydes for the co-oxidation.

In the present invention, it is possible to use the oxidation method using the above-mentioned organic peracids or the co-oxidation method to produce ε-caprolactone through oxidation of cyclohexanone.

Further, the oxidation or the co-oxidation may be carried out by using peracid without using a solvent for dilution. However, ethyl acetate, methyl acetate, methyl benzoate or other esters, hexane, cyclohexane, benzene, toluene or other hydrocarbons, ketones, nitriles and carboxylic acids may be given as examples of the solvent for dilution that may be used.

When an organic solvent is used, it preferably has a boiling-point lower than the boiling point of ε-caprolactone, for distillation recovering after reaction.

In the oxidation reaction of cyclohexanone by organic peracids, the organic peracid oxidises cyclohexanone (bp 155° C.) which is transformed to ε-caprolactone (bp 98–99° C./2 mm Hg). The organic peracids themselves are reduced into organic acids such as acetic acid (bp 118.2° C.), propionic acid (bp 141.35° C.), formic acid (bp 100.5° C.) and isobutyric acid respectively (bp 154.3° C.), depending on the organic peracids used. For that reason, ε-caprolactone, organic acids such as acetic acid or the like which have been synthesised by reduction and solvents for dilution are contained in the reaction mixture resulting from the oxidation of cyclohexanone. Further, adipic acid (bp 265° C./100 mmHg), hydroxycaproic acid, caprolactone oligomers and polymers which are by products are also contained in the reaction mixture. The organic acids which have been synthesised by reduction have a boiling point lower than the boiling point of ε-caprolactone ; adipic acid and hydroxycaproic acid, caprolactone oligomers and polymers have a boiling point higher than that of ε-caprolactone.

Moreover, in the oxidation reaction of cyclohexanone via co-oxidation method, the reaction may be performed under the absence or presence of a catalyst, with a molar-ratio of cyclohexanone/aldehyde=1–10, at a temperature between 0–150° C. and under a pressure ranging from atmospheric pressure to 50 kg cm$^2$. Co, Mn, Fe, Cu, Al, V, Zr, Au, Pt, Pd, Ru or other metals or metal salts thereof are used as catalyst in an amount of 0.01 ppm to 100 ppm with respect to the aldehyde amount. The catalyst can be separated by filtration after reaction or a distillation may be carried out while partially remaining the catalyst, as it will be described hereinafter.

For that reason, ε-caprolactone, carboxylic acids produced through co-oxidation of aldehydes, unreacted aldehyde(s), unreacted cyclohexanone, cyclohexene oxide, hydroxy-cyclohexanone, ring-opened polymers thereof, other compounds from oxidation of aldehyde, solvent used for dilution, adipic acid, hydroxycaproic acid, caprolactone oligomers and polymers or the like are contained in the reaction solution obtained from the co-oxidation of cyclohexanone. Carboxylic acids and ε-caprolactone are separated from the reaction mixture which is obtained as described above (reaction mixture from peroxide oxidation method, reaction mixture from co-oxidation method or mixtures thereof. When the boiling point of carboxylic acids is lower than the boiling point of ε-caprolactone, carboxylic acids may be separated through distillation. When the boiling point of the carboxylic acids is higher than the boiling point of ε-caprolactone, they can be separated through crystallisation or ion-exchange resins. It is also possible to distill ε-caprolactone out of the high-boiling fraction which remains after distillation.

Optionally, the catalyst used and reaction solvent may be separated. After separation of the produced carboxylic acids, ε-caprolactone may be purified by distillation.

It is necessary that the purity of the ε-caprolactone obtained is not less than 99.8% by weight.

When a purification by distillation is carried out, the increase of the purity level involves an increase of equipment and operation costs. It is important to reduce the concentration of any impurity even it is low, since the storage-stability of monomer and an effect for suppressing discoloration during polymerisation are then lowered.

In the present invention, investigations regarding compounds which are factors causing thermal discoloration of εcaprolactone monomer or polymer have been done. The results of these investigations are that impurities are not always specified but on the basis of the gas-chromatographic analysis described hereinafter it has been found out that the amount of components having a relative retention time not more than 0.6 with respect to the relative retention time of ε-caprolactone which is set at 1.00, must be not more than 200 ppm.

Gas chromatographic analysis conditions:
Column: strongly polar capillary column ; liquid phase DB-WAX (in replacement PEM-20M, FFAP or the like may also be used); column length : 30 m×column diameter 0.25 mm, thickness of the liquid phase
film: 0.25 μm
column temperature: constantly set at 160° C.;
carrier gas: He 1 ml/min, split ratio: 100:1;
temperature of the detecting device: 250° C.;
temperature of the inlet 250° C.

Figure 2:
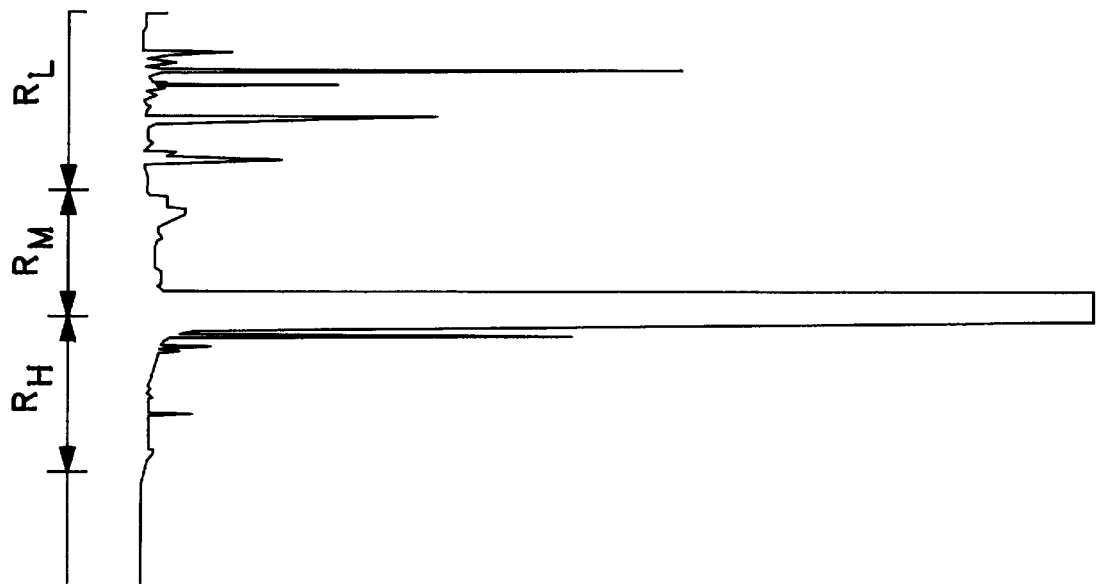
FIG. 2 shows a gas chromatograph chart of the ε-caprolactone product of Comparative Example I-1.

FIG. 1 and FIG. 2 show Examples of charts in relation to ε-caprolactone by gas-chromatography carried out under the above-mentioned analysis conditions.

Herein, the retention time of ε-caprolactone is approximately 8.4 min. When the relative retention time corresponding to relative retention time of ε-caprolactone is set at 1.00, it is necessary that the concentration of the total surface corresponding to the fraction of components having a relative retention time of not more than 0.6 (low-boiling) be not more than 200 ppm based on area ratio.

It is to be noted that, on FIGS. 1 and 2, the region corresponding to a relative retention time of not more than 0.6 is shown from the start by the portion RL, the region corresponding to a relative retention time greater than 0.6 and less than 1.0 is shown by the portion RM and the region corresponding to a relative retention time of more than 1.0 and less than 2.0 is shown by the portion RH.

In the present invention, in order to control thermal discoloration due to low-boiling components, the total concentration based on area ratio corresponding to components having a retention time of more than 0.6 and less than 1.0 (middle-boiling components except the part corresponding to the leading peak of ε-caprolactone) is preferably of 100 to 1000 ppm in a gas-chromatographic analysis under fixed conditions wherein the relative retention time of ε-caprolactone is set at 1.00.

In the present invention, in order to control thermal-discoloration due to the above-mentioned low-boiling impurities, the total concentration base on area ratio corresponding to components having a retention time of more than 1.0 and less than 2.0 (high-boiling components except the part corresponding to the leading peak of ε-caprolactone) is preferably of 100 to 1,000 ppm in a gas-chromatographic analysis under fixed conditions wherein the relative retention time of ε-caprolactone is set at 1.0.

Investigations related to the treatment of substances causing thermal-discoloration of ε-caprolactone monomers or polycaprolactones obtained through the above-described reaction have also be carried out in the present invention. Results of these investigations are that the color hue (APHA value) of ε-caprolactone obtained from purification by distillation is reduced when this distillation is carried out after heating under the presence of discoloration-improving agents or when it is carried out while heating under the presence of discoloration-improving agents polycaprolactones having an improved color hue can be also obtained by using the ε-caprolactone obtained.

Elements or compounds of groups 4A, 5A, 6A, 7A, 8, 1B and 2B are used as discoloration-improving agents.
Ti, Zr and Hf are examples of elements of group IV;
V, Nb and Ta are examples of elements of group V;
Cr, Mo and W are examples of elements of group VI;
Mn and Re are examples of elements of group VII;
Fe, Ru, Os, Co, Rh, Ir, Ni, Pd and Pt are examples of elements of group 8, 9 et 10;
Cu, Ag and Au are examples of elements of group XI;
Zn, Cd and Hg are examples of elements of group XII.

Fluorine-containing compounds, chlorine-containing compounds, bromine-containing compounds, iodine-containing compounds or other halogenated compounds, oxides, hydroxides, carboxylic acids, phenol, hydroxycarboxylic acids, para toluenesulphonic acid, or their organic salts, nitric acid, sulphuric acid, hydrochloric acid, phosphoric acid or organic and inorganic salts thereof ; hydroxyesters, alkaline metals, alkaline-earth metals, ammonia, amines or complex salts thereof may be cited as examples of discoloration-improving agents. They may be used alone or in mixture.

More specifically, titanium trichloride, titanium tetrachloride, titanium nitrate, titanium lactate ethyl ester, titanium hydroxy stearate, zirconium nitrate, zirconium-ammonium salts of acetic acid, zirconium hydroxy acetate, zirconium stearate, vanadium oxytrichloride, vanadium tetrachloride, chromium oxide, chromium chloride, chromium nitrate, chromium acetate, molybdenum oxide, ammonium molybdate, molybdenum acetylacetonate, tungstic acid. sodium manganese tungstate, manganese chloride, manganese nitrate, manganese sulphate, ferric nitrate, cobalt chloride, cobalt nitrate, cobalt acetate, nickel nitrate, nickel bromide, palladium chloride, palladium sulphate, cuprous oxide, copper chloride, copper oxalate, copper acetate, silver oxide, silver nitrate, cadmium laurate or the like can be given as examples.

The above-mentioned discoloration-improving agents are preferably added to the starting materials (starting materials in distillation) supplied into the distillation column for recovery of ε-caprolactone. The amount to be added of these agents is 0.1 to 1,000 ppm based on the weight of the starting materials, preferably 1 to 10 ppm. When the weight to be added is less than 0.1 ppm, the effect is small; when the weight amount to be added is more than 1000 ppm, the effect is not as great as expected and it is not economically interesting.

The starting materials in distillation are compounds which remain after removing optionally-used catalysts and reaction solvents from synthesised compounds and after removing synthesised carboxylic acids. Starting materials in distillation are materials from which ε-caprolactone is recovered by purification by distillation as a product.

Further, starting materials in distillation may contain deteriorated or contaminated ε-caprolactone monomers; such monomers can be treated by the present invention.

Accordingly, the discoloration-improving agents can be added in one or several steps during the distillation purification; they may be added to the starting-materials in distillation which are provided at the first stage of the distillation column for the purification by distillation but they may also be added to the solution supplied into an intermediate stage of the distillation column or added to the solution supplied into the final stage of the distillation column.

Preferably, the discoloration-improving agents are soluble in the starting-materials in distillation. As powders, they may also be dispersed therein or be fed in a packed column to make the starting materials in distillation to pass therethrough under heating.

As a result, in the present invention, it is possible to obtain ε-caprolactone having a monomer thermal-coloration value APHA of not more than 30 and preferably not more than 25. Further, it is possible to obtain ε-caprolactone monomer having a thermal-discoloration value APHA of not more than 50 after a one-week storage, Purification of ε-caprolactone is carried out by distilling out low-boiling fraction (i.e. separation by distilling out low-boiling fraction) and by distilling out high-boiling fraction (i.e. separation through letting high-boiling fraction remaining) in the above-mentioned reaction mixture.

The addition of discoloration-improving agents may be carried out during distilling-out low-boiling or during distilling-out high-fraction. The starting-material in distillation in which discoloration-improving agents have been added are heated at 20–250° C., preferably at 100° C.–160° C. Heating period of time depends on temperature. Heating period of time is approximately of 1 second at high temperature and 10 hours at low temperature.

When carrying out purification by distillation, the distillation may be carried out in one stage or multistage. Preferably, distillation is carried out in two or three stages.

During distillation, the temperature of the liquid in the bottom of the distillation column is generally set not more than 160° C. and preferably not more than 150° C. The pressure of the top of the column is then reduced. It is advantageous to reduce the pressure loss inside the column. For example, in the case of a sieve tray-type distillation column, the height of the partition formed by tray may be reduced, in the case of a packed-type distillation column, it is possible to use a stacked packing having a low pressure loss. Further, to reduce the heating time of the reboiler of the distillation column, it is possible to use a falling-film evaporator.

(1) in a two-step distillation, the reaction liquid resulting from oxidation of cyclohexanone is fed into a first distillation column and distilling out of low-boiling-fraction is then carried out. Low-boiling fraction composed of solvent for dilution, organic acids having a low boiling point and the like are distilled off with unreacted cyclohexanone.

In the present invention, the first distillation-column may be any one of a plate column or a packed column. Conditions of the first distillation such as feeding rate of reaction-liquid can be chosen as suitable according to the type of distillation column. However, generally, the temperature of the top of the column is from 20 to 60° C., particularly from 30° C. to 40° C. and the temperature of the bottom of the column is from 100 to 200° C., particularly from 120 to 180° C., the pressure at the top of the column is not more than 200 mm Hg, reflux ratio is from 0.1 to 10, preferably from 0.5 to 5. According to such distillation conditions, solvent, acetic acid and low-boiling components which includes discoloration-causing compounds are efficiently distilled off as low-boiling fraction. At the same time, the liquid of the bottom of the first distillation column which contains ε-caprolactone can be recycled from the bottom of the column. Further, ε-caprolactone is partially distilled off together with the low-boiling fraction. The ratio distilled off of ε-caprolactone is from 0.5 to 3.0%.

Then, the liquid of the bottom of the first distillation-column, which contains ε-caprolactone (hereinafter called a crude ε-caprolactone) is extracted from the bottom of the distillation-column and fed into a second distillation-column. The second distillation-column may also be any one of a plate column or a packed column but characterised in that the concentration zone has not less than three stages, preferably from 3 to 45 stages and more particularly from 10 to 35 stages. Specifically, this distillation column comprises from 5 to 50 stages, more preferably from 15 to 40 stages. In this range, distilling off low-boiling fractions which are a discoloration factors and separation of high-boiling fraction may be efficiently carried out. When the concentration zone has the above-mentioned stage number, feeding into the second distillation column may be carried out through the bottom of the second distillation column or through an intermediate stage of the second distillation column. The intermediate stage of the second distillation column means any stage of the second column except the bottom and the top thereof.

Distilling-off low-boiling and distilling-off high-components are carried out again in the second distillation column.

Conditions in the second distillation column such as feeding rate of reaction-liquid can be chosen as suitable according to the type of distillation column. However, in order to reduce the loss due to polymerisation of ε-caprolactone, the temperature of the top of the column is from 100 to 140° C., particularly from 110° C. to 130° C. and the temperature of the bottom of the column is from 120 to 200° C., particularly from 130 to 160° C., the pressure at the top of the column is not more than 50 mm Hg, reflux ratio is from 0.1 to 10, preferably from 0.3 to 5. Consequently, the middle-boiling fractions which reduce the purity of low-boiling fractions remained and low-boiling fractions which is produced in the column are efficiently distilled off from the top of the column. At the same time, it is possible to separate high-boiling components such as caprolactone oligomers or the like and adipic acid or the like which constitute the solution of the bottom of the second distillation column from ε-caprolactone.

In the present invention, the purified ε-caprolactone (an ε-caprolactone product) is extracted from any stages situated up to the feeding stage of the second distillation column and down to the top stage thereof.

The recovery of ε-caprolactone from the middle portion of the second distillation column is preferably carried out when ε-caprolactone is in a liquid state. The concentration of compounds causing discoloration in the product increases when the recovery is carried out in a state of vapour ε-caprolactone since low-boiling fractions which are dispersed inside the second distillation column are distilled out with the product.

In order to recover an ε-caprolactone product in a liquid state, the extraction of the liquid phase at the extraction stage may be carried out.

(2) In a 3 steps distillation, a two-steps distillation is carried out exactly as mentioned above. In the first distillation column, the low-boiling point fractions which are cut contain several low-boiling components, in the second distillation column, the low-boiling fractions which are cut contain a lot of middle-boiling components. Therefore, conditions in first and second distillation columns are as follows: temperature of the top of the column is lower than the temperature of the top of the first distillation column for the two steps distillation and/or the reflux ratio is increased. In the third distillation column, conditions may be the same as in the second-distillation column for the two steps distillation as explained in the above-mentioned stage (1). However, ε-caprolactone may be recovered with a reduced extraction-stage number and a reduced residence-time in heating.

Of course, ε-caprolactone is recovered in a liquid state from the middle part of the third distillation column, this product can be considered as the final product.

Further, according to the present invention, distillation before the second step may be carried out with a falling-film evaporator or a molecular distillation apparatus; the pressure of the top of the column is not more than 10 mm Hg, preferably not more than 5 mm Hg and with a suitable temperature for the liquid in the bottom of the column.

Moreover, according to the present invention, the most part of carboxylic acids which are by-produced (in case of acetaldehyde, acetic acid is by-produced and benzoic acid in case of benzaldehyde) are removed and the liquid which is to be fed in the column or the crude ε-caprolactone is heated at a temperature of not less than 150° C., preferably not less than 200° C. for not less than 1 minute and preferably for not less than 10 minutes and more preferably for not less than 1 hour before distillation or may be also distilled after adding discoloration-improving agents.

Further, according to the present invention, the most part of carboxylic acids which are by-produced may be removed and the pH of the liquid which is to be fed in the column or the pH of the crude ε-caprolactone may be adjusted to a value from 6 to 8, preferably from 6.5 to 7.5 before distillation.

Further, according to the present invention, the most part of carboxylic acids which are by-produced and the liquid to be fed into the distillation column (that is to say, a crude ε-caprolactone) or a purified ε-caprolactone may be purified over activated carbon, an absorbant such as molecular sieves and/or via passing through ion-exchange resins. Anionic ion-exchange resins, cationic ion-exchange resins may be used successively or as a mixture. They may be used in this order (anionic and then cationic) or in the opposite order (cationic and then anionic).

According to the purification method of the present invention, the purity of ε-caprolactone is not less than 99.8% by weight, acid value ranges from 0.05 to 0.20 mg KOH/g, water content ranges from 50 to 150 ppm and lower-boiling fractions are not more than 200 ppm based on area ratio, APHA is not more than 30 and preferably not more than 25 and more preferably not more than 20. Accordingly, when polymerisation is carried out using the ε-caprolactone which is a product of the invention, the reaction rate is improved and at the same time, deterioration of the ε-caprolactone product in storage can be prevented.

Polycaprolactones are used in numerous fields of production due to their average-molecular weight and the different functional groups or the like they contain. For example, ε-caprolactone oligomers and polycaprolactones having a molecular weight of 500 to 5000 and which are obtained using glycol as initiator are very useful as starting materials for polyurethanes, paints or the like. Further, polycaprolactone-modified compounds having radically polymerisable double bonds are advantageously used as acrylic-type coatings in fields such as automobiles, home electric appliances or the like. Moreover, polycaprolactones having a molecular weight of more than 10,000 have useful mechanical strength and are used in plastic moulded products, films, hot-melt adhesives or the like.

A lot of such polycaprolactones are produced via ring-opening polymerisation of ε-caprolactone, in presence of a catalyst and using a compound containing hydroxyl groups as initiator.

It is to be noted that, in the present invention, the term polycaprolactone is not limited to ε-caprolactone but also includes copolymers of polycaprolactones obtained from other lactone-monomers such as butyrolactones.

When functional groups other than hydroxyl groups are not necessary at the termini of the polycaprolactone molecule, mono-alcohol such as methanol, ethanol, n-propanol or isopropanol, each sort of butanol, phenol or the like, diol such as ethylene glycol, propylene glycol, butanediol, diethylene glycol, di-propylene glycol or the like, triols such as glycerine, trimethylol propane or the like and polyols such as neopentyl glycol, pentaerythritol or the like may be used as organic compounds having at least one hydroxyl group.

In order to use the polycaprolactones obtained as starting materials for polyurethanes, the termini of the polycaprolactone molecule have necessarily a hydroxyl group. In order to produce such polylactones ethylene glycol, butylene glycol or other diols, triols and polyols are used as initiators.

Further, it is possible to synthesise copolymers containing polycaprolactone segments by using as initiator high molecular weight compounds containing hydroxyl group(s). Polyethylene terephthalate, polybutylene terephthalate, polylactic acids or other polyesters, celluloses, polyvinyl alcohols, polysiloxanes may be given as examples. Further, alcohol-modified polyolefins may also be used. These initiators may be used alone or in a mixture of two or more kinds according to desired polycaprolactones.

Further, when functional groups other than hydroxyl groups are necessary at the termini of the polycaprolactone molecule, it is possible to use functional groups which neceassarily contain at least one active hydrogen such as, for example, a carboxylic group, amino group, epoxy group, hydrocarbon groups containing a double bond. Specifically, in order to introduce a carboxylic group, hydroxy-carboxylic acid or the like may be used; in order to introduce an amino group, diamines such as methylimino-bis-ethylenediamines or the like may be used, aminoalcohols such as N-methyidiethanolamine or the like, piperazines may be used; in order to introduce a double bonds, (meth)acrylic compounds containing an hydroxyl group such as, for example, hydroxyethyl acrylate or the like may be used.

According to the present invention, the molar ratio of initiator and ε-caprolactone may be appropriately selected according to the desired polymerisation rate. According to the present invention, it is possible to produce a variety of polycaprolactones from oligomers to polymers. The molar ratio of initiator and monomer is: initiator/ε-caprolactone and optionally other lactones=1:1 to 1:5,000, preferably 1:1 to 1:2,000.

Catalysts used for the polymerisation of ε-caprolactone in the present invention are those generally used for ring-opening polymerisation of lactones.

Specifically, lithium, sodium, potassium, rubidium, cesium, magnesium, calcium, barium, strontium, zinc, aluminium, titanium, cobalt, germanium, tin, lead, antimony, arsenic, cerium, boron, cadmium, manganese or other metallic compounds, oxides of the metals, organometallic compounds containing these metals, salts of organic acids thereof, halogenated compounds thereof and alkoxides may be given as examples of catalysts. Preferably, among these compounds, organometallic compounds, salts of organic acids, halogenated compounds or alkoxides of tin, aluminium or titanium are used and more particularly, organic tin compounds may be used.

Stannous tetra-acetate, monobutyl tin hydroxide, monobutyl tin tri-2-ethylhexanoate, dibutyl tin oxide, dibutyl tin dilaurate, tin dioctanoate or the like may be given as examples of such organic tin compounds.

Further, in the present invention, it is possible to obtain polycaprolactones having a narrow molecular-weight distribution via living polymerisation using cyclopentadienyl-type rare earth-metal complexes represented by general formula $(C_5R_5)$ aLnXb, as catalysts.

In the present invention, the above-mentioned catalysts may be used alone or as a mixture of more than two compounds thereof.

The amount of the catalyst used ranges from 0.0001 to 0.2% by weight with respect to the total amount by weight of initiator and lactones, particularly and preferably from 0.0005 to 0.05% by weight. When the amount is less than 0.0001% by weight, the reaction rate is slowed down and when it is more than 0.2% by weight, it has a bad influence on color hue and thermal stability of the synthesised polycaprolactones.

EXAMPLES

The present invention will be explained further on the basis of the following Examples. However, the present invention is not limited to these Examples. Further, regarding the terms % and ppm, when it is not particularly indicated, % refers to % by weight and ppm of impurities such as low-boiling fractions, middle-boiling fractions and high-boiling are indicated by ppm based on the area ratio of gas-chromatography chart. (measurement items)

(i) the acid value is calculated via the amount of a solution of $\frac{1}{10}$N of KOH which is necessary for neutralization when added into 1 g of an ε-caprolactone product.

(ii) the water content is measured with a Karl Fischer-type hygrometer.

(iii) gas chromatography is according to the previous method.

(iv) thermal-discoloration test of ε-caprolactone: 30 ml of ε-caprolactone are introduced in a testtube (made of glass, internal diameter of 20 mm, length of 160 mm) and then heated at 150° C. for 1 hour. A standard solution of APHA is then introduced in a similar tube and the color hue is visually compared.

(v) the color hue of polycaprolactone : a solution of xylene containing 30% of polycaprolactone is prepared and introduced into a testtube (made of glass, internal diameter of 190 mm, length of 270 mm) at a depth of 170 mm. A standard solution of APHA is then introduced in a similar tube and the color hue is visually compared.

Synthesis Example I-1

60 g/hour of cyclohexanone and 170.5 g/hour of a solution of ethyl acetate used as a solvent and containing 30% of peracetic acid (51.4 g/hour of pure peracetic acid which corresponds to 1.1 mole based on one mole of cyclohexanone) were introduced in a flowing-type reactor of 2 liters. The reaction was conducted under a reaction temperature of 50° C. The composition of the solution obtained was ε-caprolactone: 28.78%, unreacted cyclohexanone: 0.52%, unreacted peracetic acid: 1.31%, by-produced adipic acid: 0.59%, caprolactone polymers: 0.30%, acetic acid: 21.16% and ethyl acetate (which was the solvent): 47.34%.

Then, the reaction liquid was fed into the first distillation-column which was a perforated-plates column having 15 stages. Distillation of the low-boiling fraction was carried out with a temperature of the top of the column of 35° C., a temperature of the bottom thereof of 160° C., a pressure of the top thereof of 60 mmHg and a reflux ratio of 1.0; removal of solvent and removal of acetic acid were then carried out. The resulting solution was fed into the second distillation column.

Synthesis Example I-2

450 g of cyclohexanone, 1160 g of ethyl acetate used as a solvent and 0.08 g cobalt naphthanate containing 6% of Co as a catalyst were introduced in a batchwise type reactor of 2 liters. 360 g of acetaldehyde were then dropped therein for 5 hours and the reaction temperature was maintained at 40° C. 2.2 liter/hour of oxygen gas was introduced from the beginning of the acetaldehyde dropping until one hour after the end of the dropping. The composition of the solution obtained was ε-caprolactone: 10.4%, unreacted cyclohexanone: 11.7%, unreacted peracetic acid: 13.8%, unreacted acetaldehyde: 8.4%, by-produced adipic acid: 0.3%, caprolactone polymers: 0.50%, acetic acid: 21.16% and ethyl acetate which was the solvent: 55.0%.

Then, the reaction liquid was fed into the first distillation-column which was a perforated plates column having 15 stages. The distillation of low-boiling was carried out with a temperature of the top of the column of 20° C., a temperature of the base thereof of 180° C., a pressure of the bottom thereof of 170 mmHg and a reflux ratio of 1.00; removal of solvent liquid and removal of acetic acid were then carried out. The resulting liquid was fed into the second distillation column.

Synthesis Example I-3

600 g of cyclohexanone and 0.08 g of cobalt naphthanate containing 6% of cobalt as a catalyst were introduced in a semi-batch autoclave of 2 liters. 480 g/hour of 2,4-dimethylbenzaldehyde was dropped therein and oxygen gas was introduced to maintain a pressure of 20 kg/cm$^2$ ; the reaction temperature was maintained at 40° C. The composition of the solution obtained was ε-caprolactone: 13.5%, unreacted cyclohexanone: 64.5%, unreacted peracetic acid: 13.8%, unreacted 2,4-dimethylbenzoic acid: 17.2%, unreacted 2,4-dimethyl benzaldehyde: 3.5%, by-produced adipic acid: 0.4%, caprolactone polymers, formic acid, xylenol and the like.

Then, after separation and removing of high-boiling component such as remaining 2,4-dimethyl benzoic acid or the like, the liquid obtained was fed in a thin film evaporator and heated at 170° C.; the distillate was introduced in a packed column having 7 theoretical plates a top pressure of 80 mmHg and a reflux ratio of 0.5 to distill out the unreacted cyclohexanone. The liquid of the bottom of the column was then introduced in the second distillation-column.

Example I-1

319 g/hour of the liquid of the bottom of the first distillation-column which was obtained in Synthesis Example I-1 was fed in the bottom of an Oldershaw-type distillation column having 20 stages and a glass-made vacuum jacket having a diameter of 40 mm. The distillation was carried out with a temperature of the top of the column of 119° C., a temperature of the bottom of the column of 144° C., a pressure in the top of the column of 15 mmHg and a reflux ratio (R/D)=100). 80.35 g/hour of the liquid of the bottom of the second distillation-column was extracted from the bottom of the column and 3.6 g/hour of low-boiling fraction was distilled off from the top of the column. An ε-caprolactone product was extracted in a liquid state (235.05 g/hour; production yield in the second distillation-column 73.7%) from the tenth stage counted from the bottom of the second distillation-column without taking into account the bottom thereof. The results of the analysis of the quality of this ε-caprolactone product were: acid value: 0.078 mgKOH/g, water content of 70 ppm ; purity of 99.90%, thermal discoloration of APHA of 20, low-boiling fraction of 155, middle-boiling fraction of 490, high-boiling fraction of 331 ppm based on area ratio. Further, after a storage for 6 days, a thermal test was carried out. The corresponding thermal discoloration was APHA of 30. Chart 1 shows the gas-chromatographic analysis of the ε-caprolactone product.

0.1 mmol (33 mg) of $(C_5H_5)_2YCl$ (THF) was dissolved in 100 ml of toluene. 50 mmol (5.7 g) of the above-mentioned ε-caprolactone product was heated at 20° C. immediately after production, and polymerised over 3 hours. The reaction product was poured into 100 mml of methanol and a polycaprolactone was obtained as a white precipitate. After drying, the yield of polymer obtained was measured and was equal to 98%. The number-average molecular weight was Mn=125,000, the molecular weight distribution was Mw/Mn=1.78. Color hue of the polycaprolactone was of APHA of 25.

Comparative Example 319 g/hour of the liquid of the bottom of the first distillation-column, obtained in Synthesis Example I-3 was fed in the bottom of an Oldershaw-type distillation column having 20 stages and a glass-made vacuum jacket having a diameter of 40 mm. The distillation was carried out with a temperature of the top of the column of 119° C., a temperature of the bottom of the column of 144° C., a pressure in the top of the column of 20 mmHg and a reflux ratio (R/D) =100). 80.35 g/hour of the liquid of the bottom of the second distillation-column was extracted from the bottom of the column and 2.2 g/hour of low-boiling fraction was extracted from the top of the column. An scaprolactone product was extracted in a liquid state (235.05 g/hour; production yield of the second distillation column 73.7%) from the tenth stage counted from the bottom of the second distillation column without taking into account the bottom thereof. The results of the analysis of the quality of the ε-caprolactone product were: acid value: 0.10 mg KOHlg, water content of 100 ppm; purity of 99.94%, thermal discoloration of APHA of 30, low-boiling fraction of 264, middle-boiling fraction of 42, high-boiling fraction of 228 ppm based on area ratio. Further, after a storage for 6 days, a thermal test was carried out. The corresponding thermal discoloration was of APHA of 60. FIG. 2 shows the gas-chromatographic analysis of the ECaprolactone product.

0.1 mmol (33 mg) of $(C_5H_5)_2YCl$ (THF) was dissolved in 100 ml of toluene. 50 mmol (5.7 g) of the above-mentioned ε-caprolactone product was immediately after production heated at 20° C. and polymerised over 3 hours. The reaction product was poured into 100 mml of methanol and a polycaprolactone was obtained as a white precipitate. After drying, the yield of polymer obtained was measured and was equal to 98%. The number-average molecular weight was Mn=122,000, the molecular weight distribution was Mw/Mn=1.80. Color hue of the polycaprolactone was of APHA of 80.

Comparative Example I-2

323.8 g/hour of the liquid of the bottom of the first distillation-column obtained in Synthesis Example I-2 was fed in the bottom of an Oldershaw-type distillation column having 20 stages and glass-made vacuum jacket of 40 mm diameter. 85.2 g/hour of the liquid of the bottom of the second distillation-column was extracted from the bottom of the column and 3.3 g/hour of low-boiling fraction was extracted from the top of the column. An ε-caprolactone product was extracted in a vapour state (235.3 g/hour production yield of the second distillation column: 72.7%) from the fifteenth stage counted from the bottom of the second distillation column without taking into account the bottom thereof. The other operations were similar as explained in Example I-1.

The results of the analysis of the quality of the ε-caprolactone product were: acid value: 0.082 mg KOH/g, water content of 79 ppm; purity of 99.83%, thermal discoloration of APHA of 25, low-boiling fraction of 184, middle-boiling fraction of 491, high-boiling fraction of 348 ppm based on area ratio.

Example I-3

The liquid of the bottom of the first distillation-column obtained in Synthesis Example I-3 was fed in the bottom of an Oldershaw-type distillation column having 20 stages and glass-made vacuum jacket of 40 mm diameter used as a second distillation-column. The distillation was carried out with a temperature of the top of the column of 75° C., a temperature of the bottom of the column of 135° C., a pressure in the top of the column of 46 mmHg and a fixed reflux ratio of 2. The middle-boiling fraction was extracted and the bottom solution was fed into a third distillation column.

The third distillation column was an Oldershaw-type distillation column having 20 stages and a glass-made vacuum jacket of 40 mm diameter. 319 g/hour of the bottom liquid obtained thereabove was fed in this third distillation column. The distillation was carried out with a temperature of the top of the column of 119° C., a temperature of the bottom of the column of 144° C., a pressure in the top of the column of 20 mmHg and a reflux ratio (R/D)=10). 80.35 g/hour of the second solution was extracted from the bottom of the column and 2.2 g/hour of low-boiling fraction was extracted from the top of the column. An ε-caprolactone product was extracted in a liquid state (235.05 g/hour; production yield of the second distillation column: 73.7%) from the tenth stage counted from the bottom of the second distillation column without taking into account the bottom thereof. The results of the analysis of the quality of the ε-caprolactone product were:

acid value: of 0.080 mg KOH/g, water content of 80 ppm ; purity of 99.94%, thermal discoloration of APHA of 25, low-boiling fraction of 123, middle-boiling fraction of 30, high-boiling fraction of 210 ppm based on area ratio. Further, after a storage for 6 days, a thermal test was carried out. The corresponding thermal discoloration was of APHA of 40. (further, it is possible to adjust the low-boiling component ratio contained in the product by adjusting the distillation ratio of the second and third distillation column).

0.1 mmol (33 mg) of $(C_5H_5)_2YCl$ (THF) was dissolved in 100 ml of toluene. 50 mmol (5.7 g) of the above-mentioned ε-caprolactone product was heated at 20° C. immediately after production polymerised over 3 hours. The reaction product was poured into 100 mml of methanol and a polycaprolactone was obtained as a white precipitate. After drying, the yield of polymer obtained was measured and was equal to 98%. The number-average molecular weight was Mn=125,000, the molecular weight distribution was Mw/Mn=1.78. The polycaprolactone color hue was APHA of 40.

Example I-4

256 g of ethylene glycol were introduced in a 2 liter flask equipped with a stirrer, a nitrogen inlet, a thermometer and a condenser. 744 g of just-produced ε-caprolactone obtained in Example I-1 and as a catalyst, 37 mg of stannous (1)

chloride were introduced and reacted at 180° C. for 10 hours under nitrogen atmosphere.

The lactone polymer obtained has the following characteristics hydroxyl group value of 56.4 KOHmg/g, acid value of 0.64 KOHmg/g, viscosity of 219 cP at 75° C, lactone dimer of 0.04%, reaction ratio of ε-caprolactone 99.6%. The polycaprolactone obtained had a color hue of APHA of 20.

Comparative Example I-2

Except that the ε-caprolactone obtained in Comparative Example I-1 was used immediately after its production, the other operations were similar to Example 14. The color hue of the polycaprolactone obtained was APHA of 90.

Example I-5

31 g of ethylene glycol, 9699 of ε-caprolactone just obtained in Example I-1 and 10 mg of titanium (IV) butoxide as a catalyst were reacted at 170° C. as explained in Example I-3.

The ratio of remaining ε-caprolactone was not more than 1%. The color hue of a polycaprolactone obtained was APHA of 25.

Comparative Example I-3

Apart from the ε-caprolactone obtained in Comparative Example I-1 was used immediately after its production, the other operations were identical to Example I-5. The color hue of the polycaprolactones obtained was APHA of 70.

Example I-6

319 of ethylene glycol, 969 g of ε-caprolactone just-obtained in Example I-1 and 5 mg of stannic (I) chloride as a catalyst were reacted at 150° C. as explained in Example I-3.

The ratio of remaining ε-caprolactone was not more than 1%. The color hue of a polycaprolactone obtained was APHA of 30.

Comparative Example I-4

A part from the ε-caprolactone obtained in Comparative Example I-1 was used immediately after its production, the other operations were identical to Example I-6. The color hue of the polycaprolactone obtained was APHA of 55.

Example I-7

158 g of trimethylolpropane, 842 g of ε-caprolactone just-obtained in Example I-1 and 100 mg of titanium (IV) butoxide used as a catalyst were introduced in a 2 liter flask equipped with a stirrer, a nitrogen inlet, a thermometer and a condenser and reacted at 170° C. under a nitrogen atmosphere.

The ratio of remaining ε-caprolactone was not more than 1% and the color hue of the polycaprolactone obtained was APHA of 15.

Comparative Example I-5

Except that the ε-caprolactone obtained in Comparative Example I-1 was used immediately after its production, the other operations were similar to Example I-7. The color hue of the polycaprolactone obtained was APHA of 30.

Example I-8

2 g of methacrylic acid, 362 g of hydroxyethyl methacrylate, 635 g of ε-caprolactone just-obtained in Example I-1 and 50 mg of stannous (I) chloride used as a catalyst were introduced in a 2 liter flask equipped with a stirrer, a nitrogen inlet, a thermometer and a condenser and reacted at 100° C. under a nitrogen atmosphere.

The ratio of remaining ε-caprolactone was not more than 1% and the color hue of the polycaprolactone obtained was APHA of 20.

Comparative Example I-6

Apart from the ε-caprolactone obtained in Comparative Example I-1 was used immediately after its production, the other operations were identical to Example I-8. The color hue of the polycaprolactone obtained was APHA of 60.

Examples I-9 to I-13

In Examples I-4 to I-8, polycaprolactones were synthesised using a mixture of 60% by weight of the ε-caprolactone obtained in Example I-1 and 40% by weight of the ε-caprolactone obtained in Comparative Example I-1, both being used immediately after their production.

The corresponding color hue was as follows:
Example I-9 (corresponding to Example I-4): APHA 45
Example I-10 (corresponding to Example I-5): APHA 40
Example I-11 (corresponding to Example I-6): APHA 40
Example I-12 (corresponding to Example I-7): APHA 20
Example I-13 (corresponding to Example I-8): APHA 35

As another method of reducing the concentration of low-boiling component, 2,4-dimethyl benzoic acid or other high-boiling component were separated and removed from the reaction liquid obtained in Synthesis Example I-3. The resulting liquid was then fed into a thin film evaporator and the distillate was heated at 170° C. and distilled in a packed column having 7 theoretical plates. The pressure in the top of the column was 80 mm Hg, the reflux ratio was 0.5. The unreacted cyclohexanone was distilled off and the liquid of the bottom of the column was fed into a second distillation-column.

Example II-1

31 9 g/hour of the mixture of the bottom of the first distillation-column obtained in Synthesis Example I-3 and 100 ppm of palladium (I) chloride were fed into an Oldershaw-type distillation column having 20 stages and a glass-made vacuum jacket having a diameter of 40 mm. The distillation was carried out under fixed conditions: temperature of the top of the column of 119° C., temperature of the bottom of the column of 144° C., pressure of the top of the column of 15 mm of Hg, constant reflux ratio (R/D=1).85.3 g/hour of the bottom liquid was removed from the bottom of the second distillation-column and the ε-caprolactone product was recovered from the top of the column (237.1 g/hour, production yield of the second bottom liquid: 73.5%)

The results of the analysis of the quality of the ε-caprolactone product were:
acid value: 0.1 8 mg KOH/g; thermal discoloration: 25APHA.

0.1 mmol (33 mg) of $(C_5H_5)_2YCl$ (THF) was dissolved in 100 ml of toluene. 50 mmol (5.7 g) of the above-mentioned ε-caprolactone product were heated at 20° C. immediately after its production polymerised for 3 hours. The reaction product was poured into 100 mml of methanol and a polycaprolactone was obtained as a white precipitate. The polycaprolactone obtained after drying had a coloration of APHA of 40.

Example II-2

322.9 g/hour of a mixture of the liquid of the bottom of the first distillation-column obtained in Synthesis Example I-3 and 100 ppm of titanium tetrachloride were fed into an Oldershaw-type distillation column having 20 stages and a glass-made vacuum jacket having a diameter of 40 mm. As in Example II-1, distillation at a reduced pressure was carried out. 85.5 g/hour of the liquid of the second distillation-column was removed from the bottom of the column and the ε-caprolactone product was recovered from the top of the column (237.4 g/hour, production yield of the second bottom solution: 73.5%)

The results of the analysis of the quality of the ε-caprolactone product were:
acid value: 0.18 mg KOH/g; thermal discoloration: APHA of 25.

The above-mentioned ε-caprolactone product was polymerised as in Example II-1. The reaction product was poured into 100 mml of methanol and a polycaprolactone was obtained as a white precipitate. The polycaprolactone obtained after drying had a coloration of APHA of 30.

Example II-3

322.9 g/hour of the mixture of the bottom of the first distillationcolumn obtained in Synthesis Example I-3 and 100 ppm of cobalt acetate were fed into an Oldershaw-type distillation column having 20 stages and a glass-made vacuum jacket having a diameter of 40 mm. As in Example II-1, distillation at a reduced pressure was carried out. 85.2 g/hour of the liquid of the second distillation-column was removed from the bottom of the column and the ε-caprolactone product was recovered from the top of the column (237.1 g/hour, production yield of the second bottom solution: 73.5%)

The results of the analysis of the quality of the product ε-caprolactone were:
acid value: 0.1 9 mg KOH/g; thermal discoloration: APHA of 25.

The above-mentioned ε-caprolactone product was polymerised as in Example II-1. The reaction product was poured into 100 mml of methanol, and a polycaprolactone was obtained as a white precipitate. The polycaprolactones obtained after drying had a color hue of APHA of 25.

Reference Example II-1

322.7 g/hour of the mixture of the bottom of the first distillation-column obtained in Synthesis Example I-3 and 100 ppm of palladium chloride were fed into an Oldershaw-type distillation column having 20 stages and a glass-made vacuum jacket having a diameter of 40 mm. The distillation was carried out under fixed conditions: temperature of the top of the column of 119° C., temperature of the bottom of the column of 1 44° C., pressure of the top of the column of 20 mm of Hg, reflux ratio of (RID 1).85.3 g/hour of the liquid of the bottom of the second distillation-column was removed from the bottom of the column and the ε-caprolactone product was recovered from the top of the column (237.5 g/hour, production yield of the second bottom liquid: 73.6%)

The results of the analysis of the quality of the ε-caprolactone product were: acid value: 0.18 mg KOH/g ; thermal discoloration: APHA of 25.

Comparative Example II-1

0.1 mmol (33 mg) of $(C_5H_5)_2YCl$ (THF) was dissolved in 100 ml of toluene. 50 mmol (5.7 g) of the above-mentioned ε-caprolactone product were warmed at 20° C. immediately after its production polymerised for 3 hours. The reaction product was poured into 100 mml of methanol and polycaprolactone was obtained as a white precipitate. The polycaprolactone obtained after drying had a color hue of APHA of 60.

It is to be noted that ε-caprolactone obtained in the present invention may be used in a mixture with other lactone monomers such as, for example, 4-methylcaprolactone or other monomethylcaprolactone and trimethylcaprolactone, valerolactone, propiolactone, glycolides, lactides and cyclic lactones containing an heteroatom. The scope of the invention also includes such uses.

The scope of the present invention also includes polymers obtained from a mixture of the above-mentioned ε-caprolactone and other lactone monomer(s).

What is claimed:

1. ε-caprolactone having a purity of at least 99.8% by weight and having a total concentration of not more than 200 ppm based on area ratio of components having a relative retention time of not more than 0.6 for the low-boiling fraction, the relative retention time of ε-caprolactone being set to 1.00 in gas-chromatographic analysis under determined conditions.

2. ε-caprolactone having a degree of purity of at least 99.8% by weight and having a total concentration of not more than 200 ppm based on area ratio of components having a relative retention time of not more 10 than 0.6 for the low-boiling fraction and a total concentration from 100 to 1,000 ppm based on area ratio of components having a relative retention time of more than 0.6 and less than 1.0 for the middle-boiling fraction, the relative retention time of ε-caprolactone being set to 1.0 in gas-chromatographic analysis under determined conditions.

3. ε-caprolactone having a purity of at least 99.8% by weight and having a total concentration of not more than 200 ppm based on area ratio of components having a relative retention time of less than 0.6 for the low-boiling fraction; a total concentration from 300 to 1000 ppm of components having a relative retention time of more than 1.0 and less than 2.0 for the high-boiling fraction, the relative retention time of ε-caprolactone being set to 1.00 in gas-chromatographic analysis under determined conditions.

4. ε-caprolactone according to any one of claims 1 to 3, characterised in that said ε-caprolactone has a thermal discoloration value, under determined conditions of not more than APHA of 25.

5. ε-caprolactone according to any one of claims 1 to 3, characterised in that said ε-caprolactone is obtained via co-oxidation of cyclohexanone and an aromatic aldehyde(s) or via oxidation of cyclohexanone using a peracid.

6. A method of producing ε-caprolactone consisting of co-oxidizing cyclohexanone and aldehyde(s) to obtain ε-caprolactone and carboxylic acid and then recovering ε-caprolactone via distillation, said method being characterised in that degree of reduced pressure and heating in said distillation are controlled in order to obtain ε-caprolactone having a purity of at least 99.8% and having a total concentration of not more than 200 ppm based on area ratio of components having a relative retention time of not more than 0.6 for the low-boiling fraction, the relative retention time of ε-caprolactone being set to 1.00 in gas-chromatographic analysis under determined conditions.

7. A method of producing ε-caprolactone consisting of co-oxidising cyclohexanone and aldehyde(s) or oxidising cyclohexanone using a peracid to obtain ε-caprolactone and carboxylic acid(s) and recovering said ε-caprolactone via distillation, said method being characterised in that said distillation is carried out after addition of an element of selected from 4A, 5A, 6A, 7A, 8, 1B and 2B groups and/or a compound containing the element.

8. Polycaprolactone(s) having a low discolorability of less than APHA of 40 and obtained via polymerisation of ε-caprolactone according to any one of claims 1–3, 6 and 7.

9. A method of producing polycaprolactone(s) having a low discolorability of less than APHA of 40 characterised in that ε-caprolactone according to any one of claims 1–3, 6 and 7 is polymerised in the presence of an initiator and a catalyst.

* * * * *